United States Patent [19]
Sherrod

[11] Patent Number: 6,053,380
[45] Date of Patent: Apr. 25, 2000

[54] APPARATUS AND METHOD FOR AUTOMATICALLY PLACING AND REMOVING A STERILE GLOVE ON A HAND

[76] Inventor: Tony D. Sherrod, 4886 Brady Dr., Memphis, Tenn. 38116

[21] Appl. No.: 09/374,963

[22] Filed: Aug. 16, 1999

[51] Int. Cl.[7] ................................................. A47G 25/80
[52] U.S. Cl. ............................................................ 223/111
[58] Field of Search ............................. 223/111, 78, 79, 223/80

[56] References Cited

U.S. PATENT DOCUMENTS

| | | | |
|---|---|---|---|
| 3,695,493 | 10/1972 | Karr | 223/111 |
| 4,889,266 | 12/1989 | Wight | 223/111 |
| 4,915,272 | 4/1990 | Vlock | 223/111 |
| 5,058,785 | 10/1991 | Rich et al. | 223/111 |
| 5,868,290 | 2/1999 | Green, Sr. et al. | 223/111 |

*Primary Examiner*—Bibhu Mohanty
*Attorney, Agent, or Firm*—John D. Gugliotta; Michael J. Corrigan

[57] ABSTRACT

This invention is an electronically sanitized medical glove dispensing machine. Not only does the machine place the warm gloves on your hands, it also takes them off and disposes of them in a sanitary way, such as a biohazard bag. The apparatus works via a compressor and a circuit board, along with sensors, "gripper clips", small air hoses, latex gloves, and a stainless steel housing. The sanitized glove is inflated so the hand can be placed in the glove before usage. A hook grips the gloves after the medical worker is finished with them, removes them, and sanitizes them.

13 Claims, 8 Drawing Sheets

APPARATUS AND METHOD FOR AUTOMATICALLY PLACING AND REMOVING A STERILE GLOVE ON A HAND

RELATED APPLICATIONS

There are no previously filed, nor currently any co-pending applications, anywhere in the world.

BACKGROUND OF THE INVENTION

1. Field of the Invention

The present invention relates generally to a method and apparatus for dispensing gloves and, more particularly, to an apparatus that automatically places a sterile glove of the type commonly used in a hospital operating room on the hands of the user by simply inserting the hand into a pair of openings located on the front of the apparatus.

2. Description of the Related Art

While the need for good old fashion hygiene has never been out of style, the needs and requirements of the medical profession have very stringent standards for reasons of health and safety. Gradually, due to increased incidents of contamination, food processors are adopting stricter standards in order to minimize such problems. As envisioned by the inventor, the Sani-Hands is intended to make such hygiene routine, easy, and consistent.

As conceived, the invention is an electronically sanitized medical glove-dispensing machine. Not only does the machine place the warm gloves on an individual's hands, but it also assists in the removal and disposal as well in a sanitary manner, utilizing a biohazard bag. The apparatus works with a compressor and a circuit board, along with sensors, "gripper" clips, small air hoses, latex gloves, and a stainless steel housing.

The sanitized glove is inflated so that the hand can be placed in the glove before usage; a hood grips the glove after the user is finished with them, allowing for easy removal and disposal.

In the related art, there exists several patents for methods and devices for dispensing a glove while shielding the remaining gloves in the dispenser from contamination. However, the art is completely devoid of any devices where sanitary gloves are dispensed and automatically placed on the hands of the user and then removes them after use. The present invention is such a device.

A search of the prior art did not disclose any patents that read directly on the claims of the instant invention; however, the following references were considered related:

| U.S. Pat. No. | Inventor | Issue Date |
| --- | --- | --- |
| 5,816,440** | Shields et al. | Oct. 6, 1998 |
| 5,392,974** | Johnson-Rabbett | Feb. 28, 1995 |
| 4,997,105** | Fischer | March 5, 1991 |
| 4,951,815** | Ulbrich | Aug. 28, 1990 |
| 4,773,532* | Stephenson | Sep. 27, 1988 |
| 4,034,853* | Smith | July 12, 1977 |
| 5,740,943* | Shields et al. | April 21, 1998 |
| 3,372,799* | Abildgaard | Mar. 12, 1968 |

SUMMARY OF THE INVENTION

It is therefore an object of the present invention to provide an automated glove dispensing and removal machine.

It is another object of the present invention to provide the sanitary application of gloves on the hand of the user.

It is yet another object of the present invention to provide for the sanitary removal of gloves from the hands of the user and dispose of them in a biologically safe manner.

It is a feature of the present invention to pre-warm gloves before placing on the hands of the user.

It is yet another feature of the present invention to allow for the easy fitting of gloves on the hands of the user.

It is still yet another feature of the present invention to prevent cross-contamination of gloves.

Briefly described according to one embodiment of the present invention, a Sani-Hands automated glove dispenser is provided utilizing a series of existing technologies in a novel manner to maintain a sanitary environment. A stainless steel housing contains all the equipment necessary to house the necessary parts in a small, portable, and permanent manner. Removal hooks are provided made of stainless steel, as well the inflation tubes. A support ring, designed to allow for the placement of a glove opening in a manner to allow fluid communication with the inside of the glove, also supports the inflation tubes and allows the tubes to be directed into the glove. Sterilized compressed air can then be provided to allow for "inflation" of the mounted glove in a manner that allows the user to insert a hand.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

LIST OF REFERENCE NUMBERS

| 10 | Sani-Hands Automated | 32b | Pin |
|---|---|---|---|
|  | Glove Dispenser | 32c | Elongated Slot |
| 11 | Door Panel | 33 | Sliding Inflation Nozzle |
| 11a | Aperture | 34 | Fixed Inflation Nozzle |
| 11b | Aperture | 34a | Bracket |
| 12 | Sidewall | 35 | Sliding Inflation Nozzle |
| 13 | Top Sidewall | 36 | O-Ring with Tab |
| 14 | Door Panel | 37 | Housing Sidewall |
| 14a | Aperture | 37a | Aperture |
| 15 | Sidewall | 38 | Trim Ring |
| 15a | Sidewall Access Panel | 40 | Hydraulic Lift |
| 16 | Bottom Sidewall | 50 | Circuit Board |
| 17 | Bio Hazard Waste Bin | 51 | Control Panel |
| 18a | Divider | 52 | Glove Applicator Sensor |
| 18b | Divider | 53 | Glove On Sensor |
| 19 | Applicator Enclosure | 54 | Removal Sensor |
| 20 | Compressor | 55 | Heating Coils |
| 21 | Tubing | 56 | Disinfectant Unit |
| 30 | Glove Applicator Assembly | 60 | Removal Cuff |
| 31 | Housing | 70 | Glove Box |
| 32 | Support Ring | 71 | Pre-packed Glove |
| 32a | Annular Slot |  |  |

DESCRIPTION OF THE PREFERRED EMBODIMENTS

The best mode for carrying out the invention is presented in terms of its preferred embodiment, herein depicted within the Figures.

1. Detailed Description of the Figures

Figure 1:
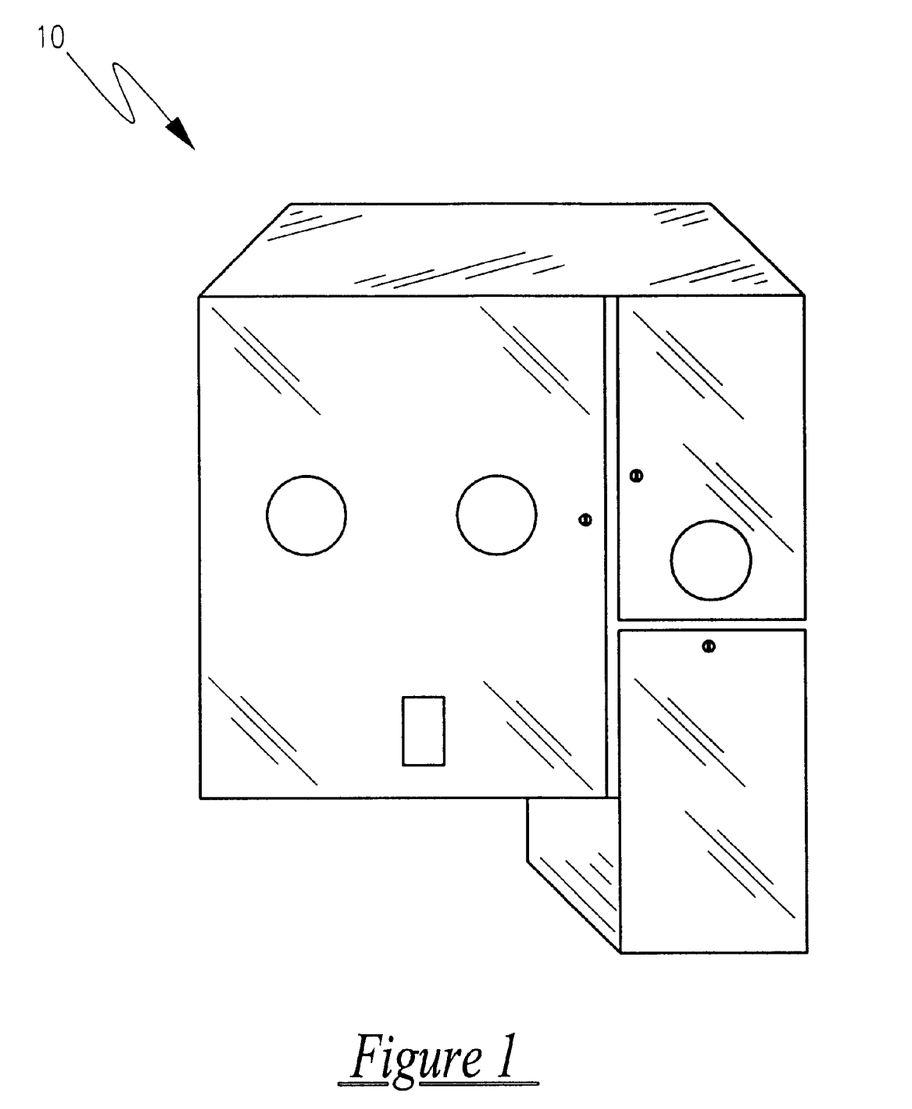
FIG. 1 is a front view of a Sani-Hands automated glove dispenser.
Figure 2:
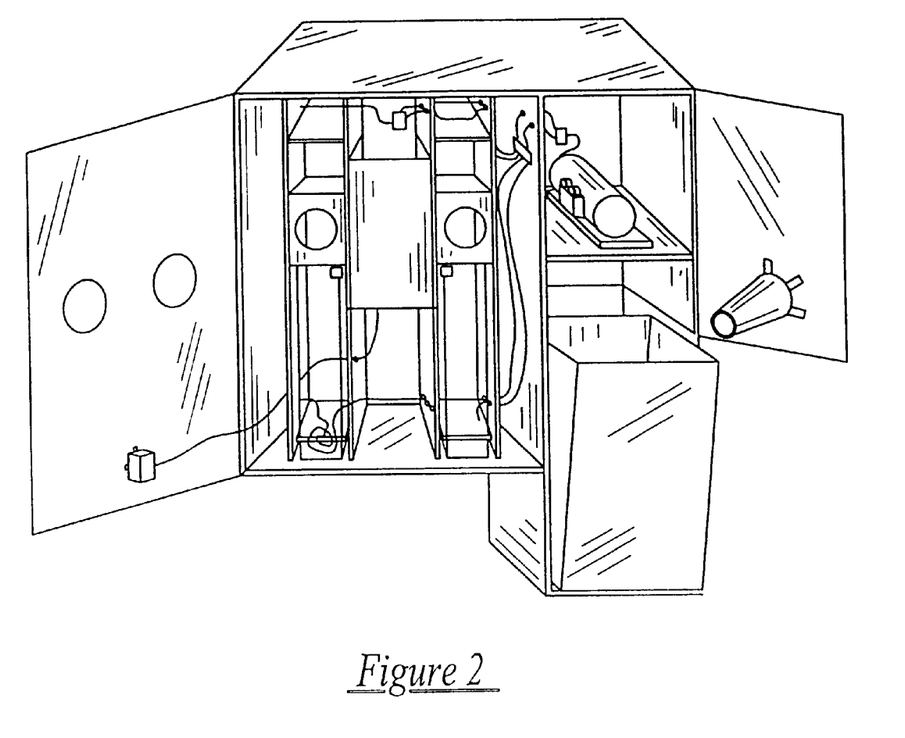
FIG. 2 is a front view of a Sani-Hands automated glove dispenser with the doors of the stainless steel housing in the open configuration exposing the main components of the device, according to the preferred embodiment of the present invention.
Figure 3:
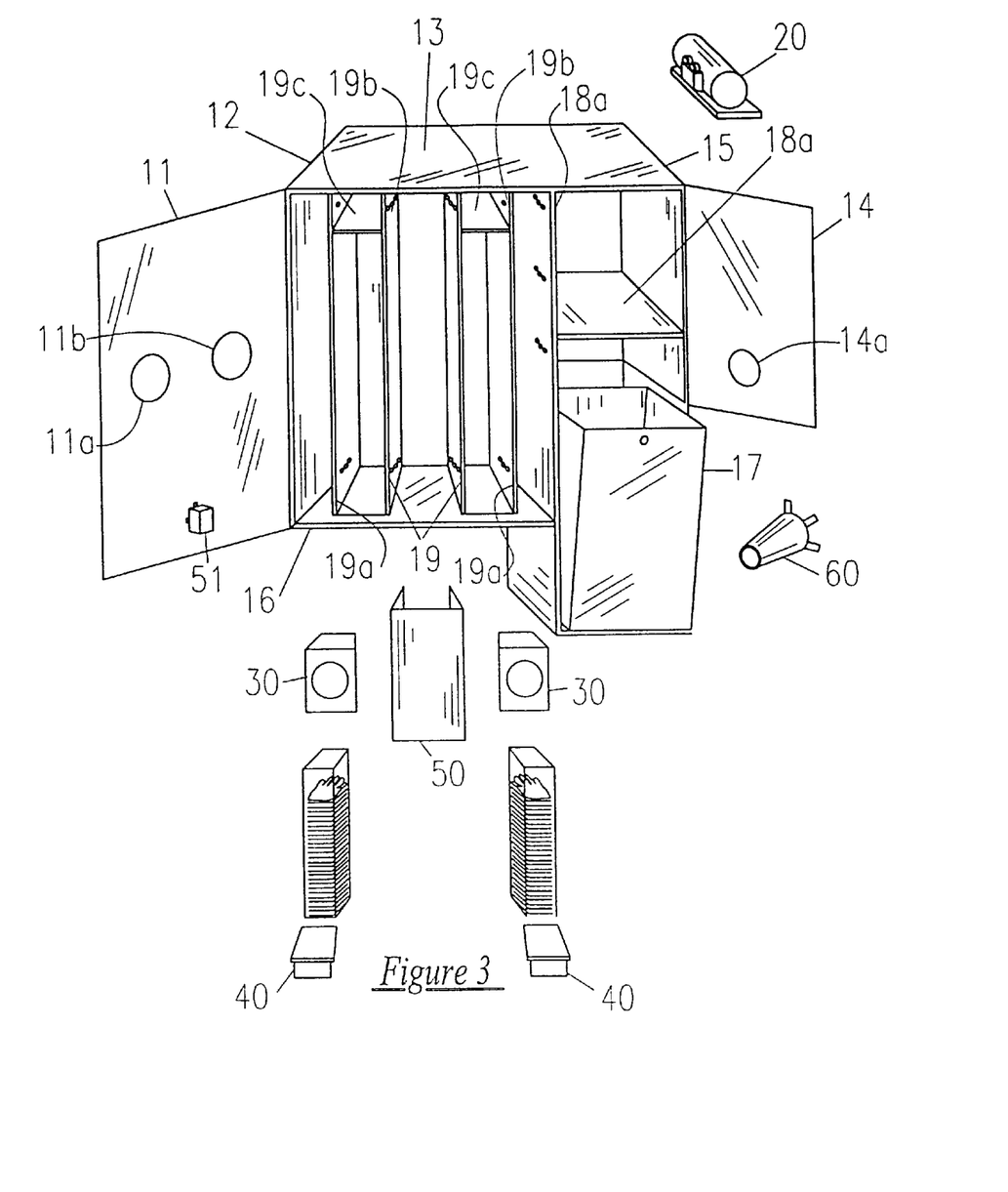
FIG. 3 is an exploded front view of a Sani-Hands automated glove dispenser with the doors of the stainless steel housing in the open configuration and the main components of the device removed, according to the preferred embodiment of the present invention.

Referring now to FIGS. 1, 2 and 3, shown is a front view of a Sani-Hands 10 automated glove dispenser. The Sani-Hands automated glove dispenser 10 is contained in a housing bolted or welded together from sheets of conventional stainless steel. The housing consists of a door panel 11, left sidewall 12, top sidewall 13, door panel 14, right sidewall 15, and bottom sidewall 16. A pair of apertures 14a formed in door panel 11 allows a user to insert their hands into the interior of the housing and into the glove applicator assemblies 30. An aperture 14a is formed in door panel 14 to allow one to insert a gloved hand into the housing and into removal cuff 60. A biohazard waste bin 17 located in the bottom right side of the housing and directly beneath removal cuff 60 is provided to catch gloves just removed by removal cuff 60. Biohazard waste bin 17 is hingably attached along the lower front edge so that biohazard waste bin 17 can be tilted forward to allow for cleaning and removal of bio waste. An elongated semi-circular slot located in the outer sidewall of biohazard waste bin 17 is provided for slidably receiving a pin fixed to sidewall 15 to ensure alignment and a smooth back and forth tilting motion of biohazard waste bin 17.

The Sani-Hands housing is further segregated into several compartments for containing various components of the invention. Divider 18a vertically segregates the housing into two main compartments. The compartment on the right is further divided horizontally by divider 18b just above the area where removal cuff 60 must protrude into the housing from door panel 14. Divider 18b also serves as a surface whereby compressor 20 is permanently mounted. The other main compartment of the housing is further segregated by two identical applicator enclosures 19. Applicator enclosures 19 are comprised of two vertical sidewalls 19a and 19b made from stainless steel and separated by another sidewall 19c. Applicator enclosures 19 are placed parallel to each other in the housing and separated by a gap. One of said glove applicator assembly 30 is located in each of said enclosures 19 within the gap formed between sidewalls 19a and 19b and positioned so that the circular aperture 37a on the front of glove applicator assembly 30 is aligned concentrically with the respective circular aperture 11a or 11b formed through door panel 11.

Located just beneath each of said glove applicator assemblies 30 is an area in which a box of sanitized pre-packaged latex or rubber gloves is inserted. The gloves are packaged flat, one on top of another, and so that the finger ends of the glove all face the rear of the box in which they are packaged. The box has a rip off top which allows one glove at a time to be removed through the top of the box. A just opened box of gloves is inserted in the area just described directly beneath each of said glove applicator assemblies. The top of each box is inserted into the bottom of each of said glove applicator assembly which is designed to receive as such. The box of gloves is sized such that it will fill the area beneath the glove applicator assembly except for a small area underneath the box and the bottom sidewall to allow room for hydraulic lift assembly 40. The bottom of the box 70 must also be designed so that as the gloves are emptied one by one from the top of the box 70, the remaining gloves are pushed into position for feeding into the glove applicator assembly 30 by the hydraulic lift 40 underneath the stack of remaining gloves 71. This requires the hydraulic lift 40 to push through the bottomwall of the box 70 that gloves 71 come pre-packaged in. It is envisioned that the box 70 bottomwall would be perforated to allow for easy ripout and the interior of box 70 would have a sanitary liner which would remain intact as hydraulic lift 40 travels through box 70 from the bottom towards the top.

For removing gloves from a gloved hand after use, a removal cuff 60 is located on the inner surface of door panel 14 mounted over aperture 14a formed therethrough specifically for said removal cuff 60.

Located on the inner surface of door panel 11 and protruding therethrough is control panel 51 housing an on/off switch for the glove applicator assemblies, heating coils, and removal cuff. Located between enclosures 19 is circuit board 50 containing various microelectronics for controlling the operation of the glove applicator assemblies and sensors, disinfectant dispenser, cuff removal assembly and sensor, heating coils, and compressor 20.

Figure 4:
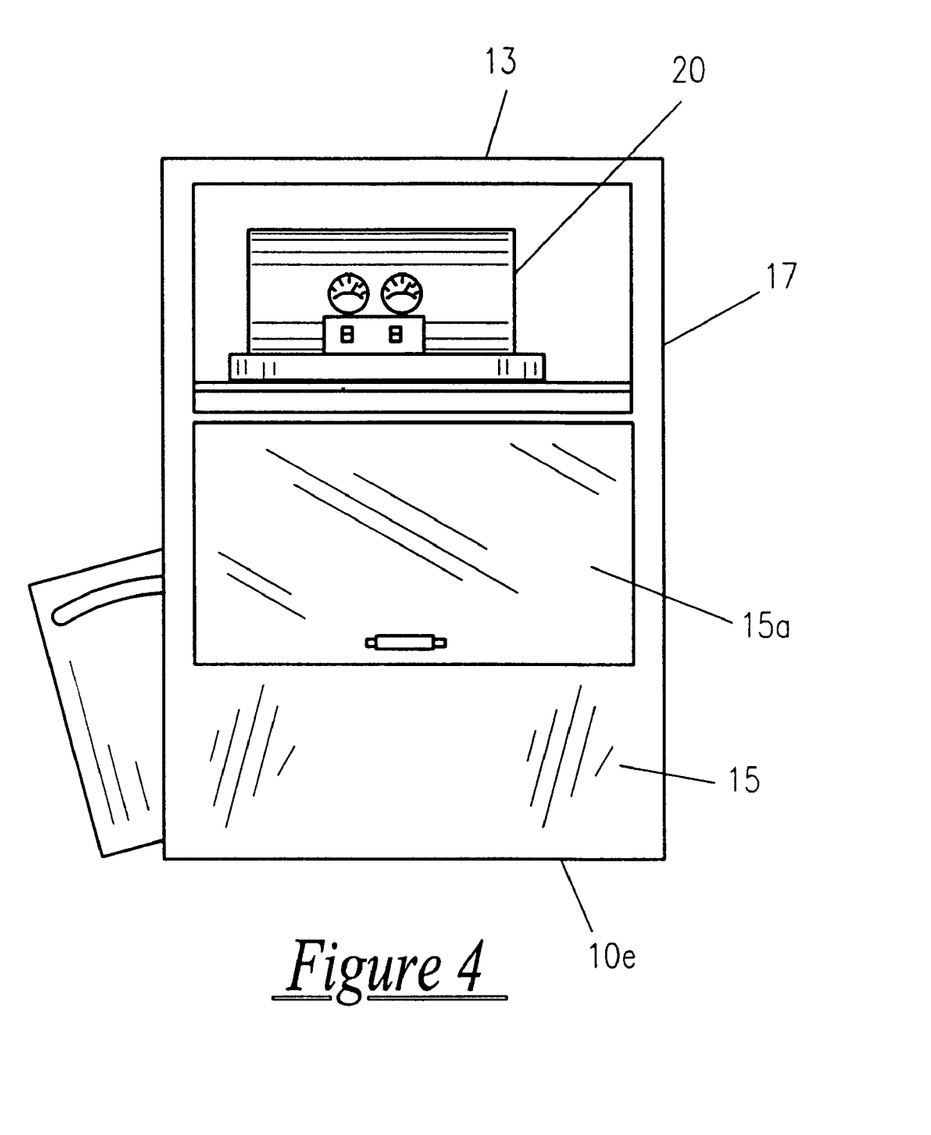
FIG. 4 is a left side view of a Sani-Hands automated glove dispenser with the side access door of the stainless steel housing in the open configuration exposing the compressor, according to the preferred embodiment of the present invention.

Referring now to FIG. 4, shown is a side view of a Sani-Hands automated glove dispenser is showing the sidewall access panel 15a in the open configuration giving accessibility for service to compressor 20. Compressor 20 may also be fitted with various gauges for monitoring pressure being supplied to the various pneumatic devices. In operation, sidewall access panel 15a would normally be in the closed configuration which is done by sliding sidewall access panel 15a upward until it engages a latch or other similar mechanism. It is envisioned that sidewall access panel may also be fitted with a keyed lock to prevent unauthorized entry and access to compressor 20. Also shown is biohazard bin 17 in the open configuration. The elongated semi-circular slot formed in the sidewall of biohazard bin 17 can also be seen in greater detail.

Figure 5:
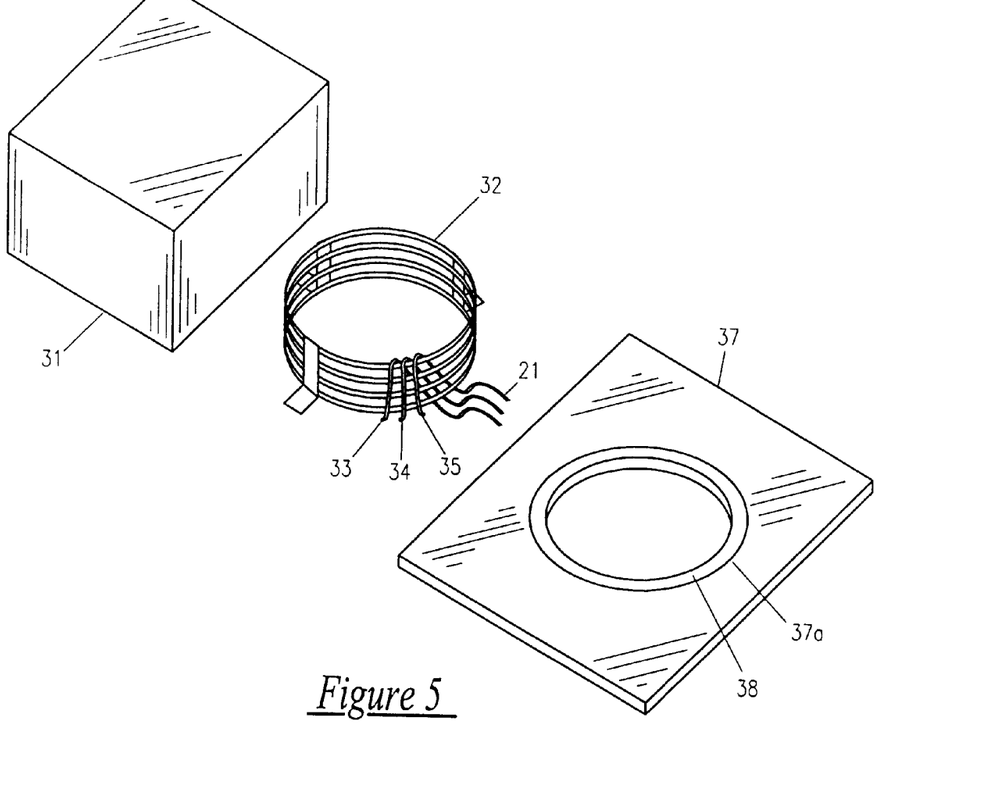
FIG. 5 is an exploded perspective view of the automated glove applicator assembly, according to the preferred embodiment of the present invention.

Referring now to FIG. 5, shown is an exploded view of a typical glove applicator assembly 30 consisting of a stainless steel housing 31, a support ring 32, a housing forward sidewall 37, trim ring 38, glove applicator sensor 52, and glove on sensor 53. Trim ring 38 is located on the outer surface of housing forward sidewall 37 positioned concentrically over an aperture 37a specifically formed therethrough. Mounted on the inner surface of housing forward sidewall 37, and discussed in greater detail in the following paragraph, is support ring 32.

Figure 6:
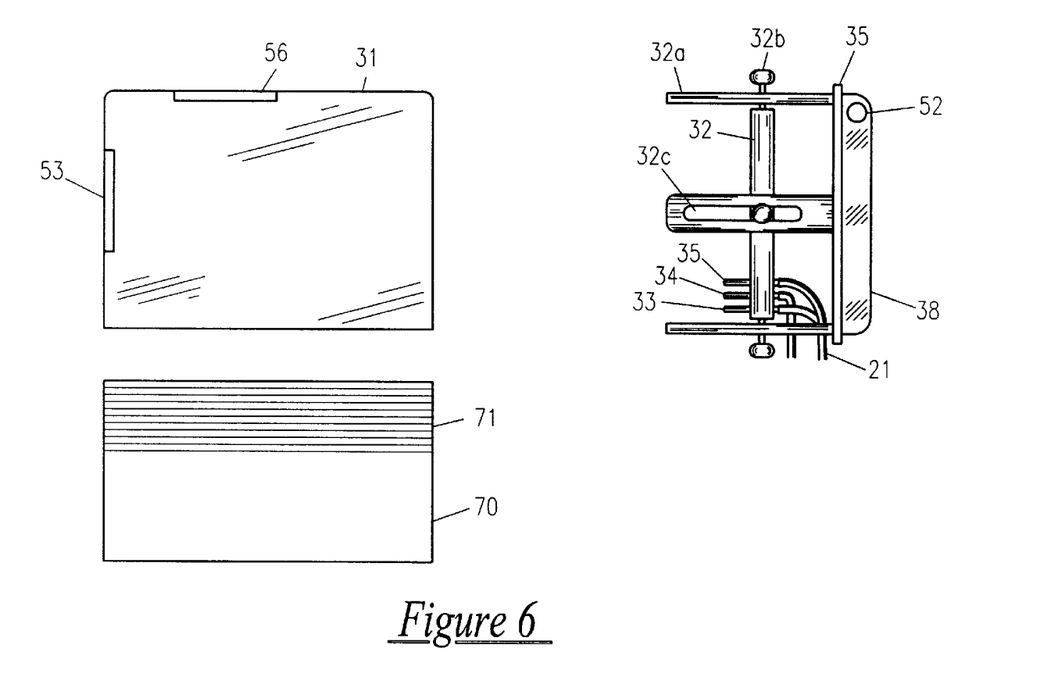
FIG. 6 is an exploded side view of the automated glove applicator assembly, according to the preferred embodiment of the present invention.

Referring now to FIG. 6, shown is side view of glove applicator assembly 30 removed from housing 31. Support ring 32 is of a multi-piece band construction so that it can radially expand and contract as support ring 32 is pushed into and pulled out of the mouth of a glove 71. A plurality of tabs 32a protruding perpendicularly from the inner surface of housing forward sidewall 37 providing the framework for mounting support ring 32. This is accomplished via an elongated slot 32c formed in each of said tabs 32a for receiving pin 32b with an elongated shaft protruding radially from the outer circumference of support ring 32. In this manner, support ring 32 is free to traverse linearly in a forward and backwards motion the length of the aforementioned elongated slots 32c. Support ring 32 is also free to radially expand and contract as the elongated shaft of pins 32b slide perpendicularly through said elongated slots 32c in tabs 32a. It is envisioned that a small electromechanical solenoid and linkages mounted on support ring 32 would provide the necessary mechanical force to effect the cyclic compression and expansion of support ring 32 as well as the linear insertion and retraction of support ring 32 into the open mouth of a glove 71. The entire sequence is activated by a motion sensitive glove applicator sensor 52 mounted on the inner circumference of trim ring 38. A box of pre-packed sanitary gloves is pre-loaded beneath housing 31 and protrudes into housing 31 through the open bottom. It is envisioned that a simple mechanism to grab the top most glove would be devised and prepare it for insertion onto support ring 32. This mechanism would be triggered by glove application sensor 52. At the same time, compressor 20 along with heating coils 55 are activated for supplying warm pressurized air to inflation nozzles 33, 34, 35. Heating coils 55 may be located anywhere along the supply tubing between the compressor 20 and inflation nozzles 33, 34 and 35. Since inflation nozzle 34 is fixed, it will remain stationary while the pressurized air is on. The other two nozzles, 33 and 35, are free to rotate radially around the inner circumference of support ring 32 since they are only slidably attached to support ring 32 via an o-ring with tab 36 slidably inserted into an annular slot 32d on the inner circumference of support ring 32. It is envisioned that a small aperture located in the lower side of inflation nozzle 33 and 35, directed downward, would provide the necessary force to propel the aforesaid nozzles radially around the inner circumference of support ring 32 so that when pressurized, inflation nozzles 33, 34 and 35 would be spaced evenly radially around support ring 32. Rubber tubing would carry pressurized air from the compressor to inflation nozzles 33, 34 and 35. At the same time, support ring 32 would begin to expand and move toward the rear of housing 31 for engaging the mouth of a glove now being fed to it as heretofore described. It is envisioned that support ring 32 could be fitted with "gripper clips" to engage the narrow bead at the mouth of a glove. Warm, pressurized air coming from the ends of nozzles 33, 34, and 35 would enter and inflate the glove allowing the user's hand to enter the glove more easily. As the user's hand fully enters the glove, the longest finger of the hand would come into contact with a pressure sensitive sensor 53 located on the rear sidewall of housing 31. This would signal to the control circuitry that the glove is on the users hand and the hand is exiting glove applicator assembly 30. Now the entire cycle reverses with the supply air slowly being turned off to nozzles 33, 34, and 35, support ring 32 contracting and being drawn back toward front housing sidewall 37. The now deflating glove will cling to the user's hand and the mouth of the glove will pull free from the now contracted support ring 32 and "gripper clips" if so equipped.

A disinfectant unit 56 can also be installed within housing 31 to dispense a small atomized dose of a strong disinfectant at periodic intervals to ensure the entire gloving procedure remains sterile.

Figure 7:
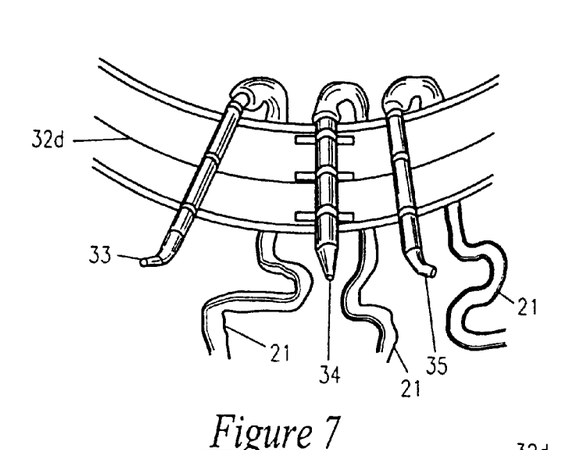
FIG. 7 is a cutaway perspective view of the inflation nozzles on the lowermost portion of the support ring, according to the preferred embodiment of the present invention.
Figure 8:
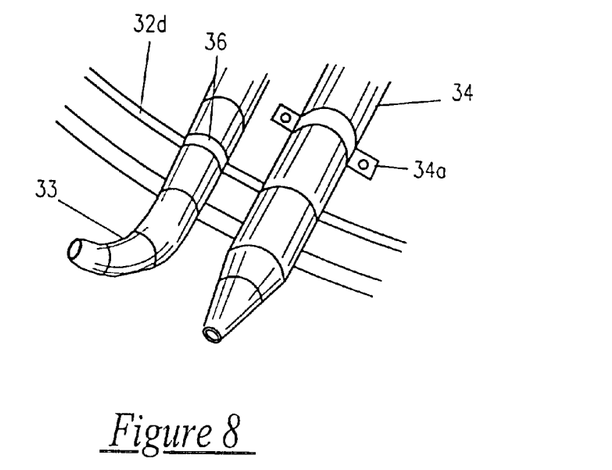
FIG. 8 is a cutaway perspective view of the inflation nozzles on the lowermost portion of the support ring showing the detail of the fixed center nozzle and the adjacent sliding nozzle slidable fixed in the annular slot, according to the preferred embodiment of the present invention.
Figure 9:
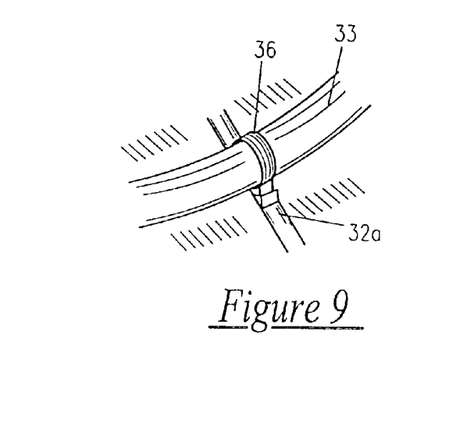
FIG. 9 is a cutaway perspective view showing the detail of one of the sliding inflation nozzles slidably attached to the support ring via an o-ring with a tab portion inserted in the annular slot, according to the preferred embodiment of the present invention.

Referring now to FIGS. 7, 8 and 9, shown are cutaway views of the lowermost portion of support ring 32 showing the detail of the attachment of inflation nozzles 33, 34, and 35. Inflation nozzle 34 is permanently attached to support ring 32 via bracket 34a. Nozzles 33 and 35 are slidably affixed to support ring 32 via an o-ring with tab 36 inserted in an annular groove on the inner circumference of support ring 32. O-ring 36 is designed to encircle the outer circumference of said nozzles 33 and 35 thereby holding said nozzles close to the inner circumference of support ring 32.

Figure 10:
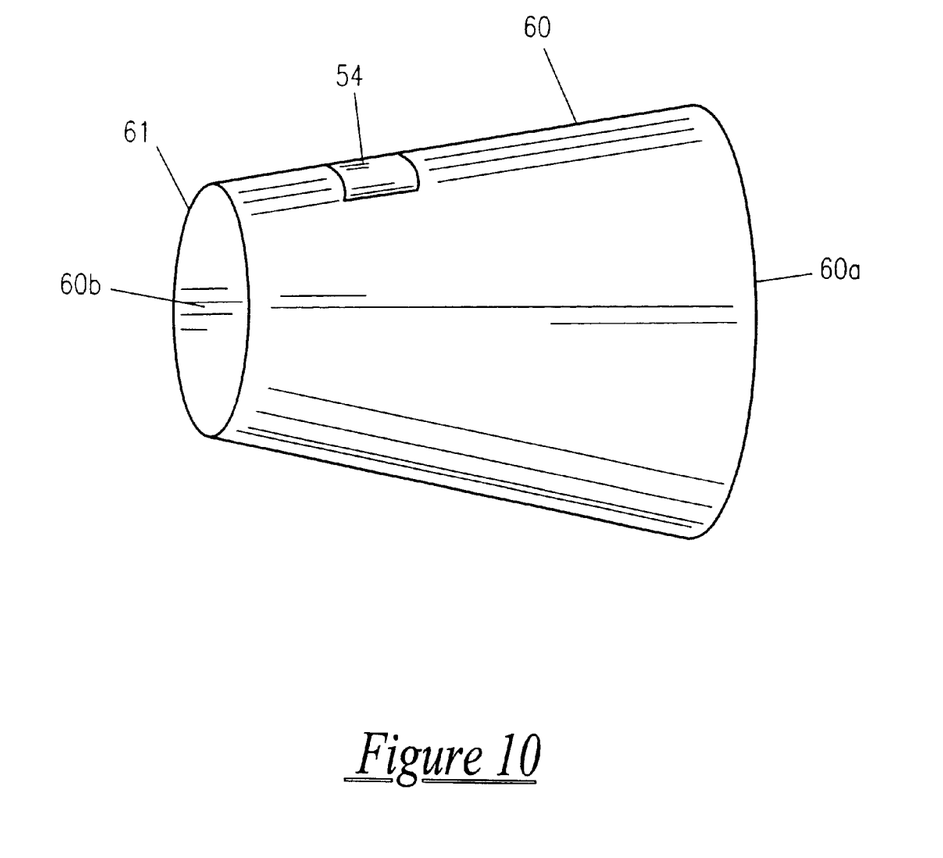
FIG. 10 is a side view of a removal cuff assembly, according to the preferred embodiment of the present invention.

Referring now to FIG. 10, shown is a side view of a removal cuff 60 made from sterile molded rubber or plastic and having a truncated cone shape with a hollow center and an elongated longitudinal axis. Removal cuff 60 has a larger aperture 60a at one end tapering to a smaller aperture 60b at the other end. A plurality of "gripper clips" line the circumference of aperture 60b. Gripper clips 61 face inwardly toward the center of aperture 60b. Gripper clips 61 are pivotally attached to the outer circumference of aperture 60b and have two positions. The first position being open, and the second being closed. In the open position, gripper clips 61 would be retracted away from the center of aperture 60b. Uin the closed position, gripper clips 61 would be aligned and facing towards the center of aperture 60b. Gripper clips 61 are designed to work in unison with each other so that when one gripper clip 61 is in the closed position, all gripper clips 61 would be in the closed position. It is envisioned that an electromechanical solenoid would move gripper clips 61 back and forth into the open and closed positions when signaled by the control circuitry located on circuit board 50. A motion sensor located on the inner sidewall of removal cuff 60 would give indicia to gripper clips 61, normally in the open position, when to close. It is desired that gripper clips 61 would close just after a gloved hand would pass through aperture 60b. The now closed grippers 61 are designed to grip the narrow bead on the mouth of a glove and hold it tightly. As a user begins to withdraw the hand from the cuff, sensor 54 detects this motion and signals gripper clips 61 to retract to the open position. The retracting gripper clips 61 pull the mouth of the glove 71 from around the user's wrist and allow the user to pull the hand from within the glove. The user now completely removes their hand from removal cuff 60. The now opened gripper clips 61 have opened sufficiently so that the grip on the bead of glove 71 is lost and glove 71 falls to the biohazard waste bin 17 below. The procedure is repeated for the other gloved hand.

The foregoing description is included to illustrate the operation of the preferred embodiment and is not meant to limit the scope of the invention. The scope of the invention is to be limited only by the following claims.

What is claimed is:

1. An apparatus and method for automatically placing and removing a sterile glove on a hand, comprising:

a housing, said housing comprising of a glove application door panel, a left sidewall, top sidewall, glove removal door panel, right sidewall, and bottom sidewall bolted or welded together from sheets of stainless steel;

a compressor, a glove applicator assembly, said glove applicator assembly consisting of a stainless steel housing, support ring, a housing forward sidewall, trim ring, glove applicator sensor, and glove on sensor;

a circuit board, a plurality of heating coils, a removal cuff, said removal cuff located on an inner surface of said door panel mounted over an aperture formed therethrough specifically for removing gloves from a gloved hand after use;

a biohazard waste bin, said biohazard waste bin located in the bottom right side of said housing and directly beneath said removal cuff for catching gloves just removed by said removal cuff;

and a hydraulic lift for supporting gloves.

2. The apparatus and method for automatically placing and removing sterile gloves on the hand of claim 1, wherein said housing is segregated by a vertical divider, said divider vertically segregating said housing into a left and right compartment;

a pair of applicator enclosures, said applicator enclosures being installed in said left compartment and each being comprised of two vertical sidewalls made from stainless steel separated by another sidewall and whereby said applicator enclosures are placed parallel to each other in said housing separated by a gap;

a horizontal divider, said horizontal divider dividing said right compartment into an upper volume and a lower volume wherein said compressor is located within said upper volume and said horizontal divider also serves as a surface whereby said compressor is permanently mounted, and further, said lower volume is adapted to receive said biohazard bin.

3. The apparatus and method for automatically placing and removing sterile gloves on the hand of claim 1, wherein a pair of apertures are formed in said glove applicator door panel to allow a user to insert their hands into the interior of said housing and into said glove applicator assemblies.

4. The apparatus and method for automatically placing and removing sterile gloves on the hand of claim 3, wherein an aperture is formed in said glove removal door panel to allow one to insert a gloved hand into said housing and into said removal cuff.

5. The apparatus and method for automatically placing and removing sterile gloves on the hand of claim 4, wherein one of said glove applicator assembly is located in each of said enclosures within the gap formed between said sidewalls and positioned so that the circular aperture on the front of said glove applicator assembly is aligned concentrically with the respective circular aperture formed through said door panel.

6. The apparatus and method for automatically placing and removing sterile gloves on the hand of claim 5, wherein said biohazard waste bin is hingably attached along a lower front edge so that said biohazard waste bin can be tilted forward to allow for cleaning and removal of bio waste, and further, wherein an elongated semi-circular slot located in an outer sidewall of said biohazard waste bin is provided for slidably receiving a pin fixed to said sidewall to ensure alignment and a smooth back and forth tilting motion of said biohazard waste bin.

7. The apparatus and method for automatically placing and removing sterile gloves on the hand of claim 6, wherein said glove applicator assembly is comprised of:

a stainless steel housing;

a housing forward sidewall;

a trim ring, said trim ring located on an outer surface of said housing forward sidewall and positioned concentrically over an aperture specifically formed therethrough;

a support ring, said support ring mounted on an inner surface of said housing forward sidewall.

8. The apparatus and method for automatically placing and removing sterile gloves on the hand of claim 7, wherein said support ring is of a multi-piece band construction so that it can radially expand and contract as said support ring is pushed into and pulled out of the mouth of said sterile glove and wherein warm, pressurized air coming from the ends of a plurality of inflation nozzles mounted on said support ring would enter and inflate said sterile glove allowing the user's hand to enter said sterile glove more easily.

9. The apparatus and method for automatically placing and removing sterile gloves on the hand of claim 8, wherein a plurality of tabs protruding perpendicularly from said inner surface of said housing forward sidewall provide the framework for mounting said support ring and wherein an elongated slot formed in each of said tabs receives a pin with an elongated shaft protruding radially from the outer circumference of said support ring so that said support ring is free to traverse linearly in a forwards and backwards motion the length of said elongated slots.

10. The apparatus and method for automatically placing and removing sterile gloves on the hand of claim 9, wherein said support ring is free to radially expand and contract as said elongated shaft of said pins slide perpendicularly through said elongated slots in said tabs, and wherein a small electromechanical solenoid and linkages mounted on said support ring provide the necessary mechanical force to effect a cyclic compression and expansion of said support ring as well as a linear insertion and retraction of said support ring into the open mouth of a sterile glove.

11. The apparatus and method for automatically placing and removing sterile gloves on the hand of claim 10, wherein the glove application sequence is activated by a motion sensitive glove applicator sensor mounted on an inner circumference of said trim ring and wherein a box of pre-packed sterile gloves is pre-loaded beneath said housing and protrudes into said housing through an open bottom.

12. The apparatus and method for automatically placing and removing sterile gloves on the hand of claim 11, wherein a simple mechanism to grab the top most glove from a box of sterile pre-packed gloves prepares said sterile gloves for insertion onto said support ring and is triggered by said glove application sensor, and wherein, at the same time, said compressor along with a heating coil are activated for supplying warm pressurized air to said plurality of inflation nozzles.

13. The apparatus and method for automatically placing and removing sterile gloves on the hand of claim 12, wherein said plurality of inflation nozzles include:

a center inflation nozzle, said center inflation nozzle being fixed and remaining stationary while pressurized air is on;

a pair of sliding nozzles, said pair of sliding nozzles being free to rotate radially around an inner circumference of said support ring since said nozzles are slidably attached to said support ring via an o-ring with an attached tab slidably inserted into an annular slot on an inner circumference of said support ring, and wherein a small aperture located in a lower side of said sliding inflation nozzles is directed downward to provide the necessary force to propel said sliding nozzles radially around said inner circumference of said support ring so that when pressurized, said sliding inflation nozzles are spaced evenly radially around said support ring; and wherein rubber tubing carries pressurized air from said compressor to said center inflation nozzle and said pair of sliding nozzles.

* * * * *